United States Patent [19]
MacCready, Jr.

[11] Patent Number: 6,086,518
[45] Date of Patent: Jul. 11, 2000

[54] SQUEEZABLE EXERCISER

[75] Inventor: Paul B. MacCready, Jr., Pasadena, Calif.

[73] Assignee: Aerovironment, Inc., Monrovia, Calif.

[21] Appl. No.: 08/848,595

[22] Filed: Apr. 28, 1997

[51] Int. Cl.[7] .................................................. G01L 5/02
[52] U.S. Cl. ................... 482/44; 482/44; 482/49
[58] Field of Search .......................... 482/49, 122, 126, 482/44, 121, 127

[56] References Cited

U.S. PATENT DOCUMENTS

| | | |
|---|---|---|
| 770,336 | 9/1904 | Terry . |
| 1,557,341 | 10/1925 | Scalbom . |
| 3,442,132 | 5/1969 | De Mare . |
| 3,670,573 | 6/1972 | Kroemer .................................. 482/49 |
| 3,672,219 | 6/1972 | Van Patten ................................. 482/49 |
| 3,995,492 | 12/1976 | Clynes . |
| 4,558,864 | 12/1985 | Medwedeff ............................... 482/49 |
| 4,674,330 | 6/1987 | Ellis . |
| 4,878,384 | 11/1989 | Bruhn . |
| 5,072,927 | 12/1991 | Santos . |
| 5,125,270 | 6/1992 | Kovacevic . |
| 5,222,926 | 6/1993 | Eggen . |
| 5,329,813 | 7/1994 | Lewis, Jr. . |

*Primary Examiner*—Jerome Donnelly
*Attorney, Agent, or Firm*—William W. Haefliger

[57] ABSTRACT

A squeezable exerciser comprising in combination body structure having surfaces to be squeezed relatively toward one another by application of force exerted by a user, and means associated with the body structure to produce a reference signal or signals as the level of force application reaches a preset limit or limits.

35 Claims, 9 Drawing Sheets

SQUEEZABLE EXERCISER

BACKGROUND OF THE INVENTION

This invention relates generally to exercise devices, and more particularly to a squeezable exerciser, which, for example can be squeezed by one hand to provide exercise with a feedback mechanism informing the operator when the squeezing force between the squeezed surface reaches a preselected value.

There is need for exercise devices which, when regularly used, can help improve musculature, health, and enjoyment of life. The challenge is to make the use of the device so attractive that users will tend to employ the exerciser regularly and effectively.

There is also need for a squeezable exerciser which is small, capable of being conveniently carried, and which can therefore be made always or easily available. Such a device would preferably provide immediate feedback information to the user when a particular preset force is reached, and the preset point is readily adjusted. Additionally such a device preferably would be operable not only by hand squeeze but also for many other muscles about the body. It should be usable with moving muscles as well as in a stationary isometric mode. Although the feedback information can reach the operator acoustically, a preferred embodiment employs a mechanical indication through the portion of the body touching it.

SUMMARY OF THE INVENTION

It is a major object of the invention to provide an improved, squeezable, exercise device meeting some or all of the above needs. Basically, the device comprises, in combination a) body structure having surfaces to be squeezed relatively toward one another by application of force exerted by a user, b) and means associated with the body structure to produce a reference signal or signals as the level of force application senses a preset limit or limits.

In this regard, the reference signal may be produced as the force load increases; and the signal may be a vibration, detectable for example by the user's hand.

As will be seen, in the improved device the reference signal producing means is preferably contained by the body structure, whereby the exterior of the body structure may be made smooth enabling easy storage of the device as in a bag or purse. Typically, the body structure includes two elongated bodies interconnected to be relatively squeezed toward one another.

An additional object is to provide a manually adjustable member associated with the body structure to be presented for manual adjustment to adjust the threshold level of force application at which signal or signals are detectable.

A further object is to provide, in the signal producing means, electrical circuitry including a transducer, the latter typically including an electrical contact, and at least one spring being employed to yieldably resist movement of the contact in response to squeezing of the body. As will be seen, the spring may advantageously comprise an elongated cantilever spring to provide non-linear response. The spring, contact and transducer are all preferably contained by the body structure.

Yet another object is to provide a signal producing means that includes at least one lever acting to displace the electrical contact at a locus characterized in that squeeze displacement is substantially less than contact displacement. As will be seen, the construction is such that squeeze force at a selected level may be applied along the lengths of the two elongated members. Two levers may be employed acting to displace the contact and extending relatively oppositely from the contact; each lever having a fulcrum and receiving squeeze force at a lever location closer to the fulcrum than the contact. In this regard, the elongated cantilever spring may extend generally parallel to the levers, providing extreme compactness. The spring, typically a wire, is typically U-shaped and has a return bend portion resisting movement of the contact, in response to body squeezing.

Another object is to provide for scale adjustment, as by provision of a member which is coupled to the wire and is manually adjustable in a direction parallel to the wire length to adjust wire bending, thereby to adjust the threshold level of force application at which the output signal or signals are detectable. Also, it simplifies the mechanism and provides more information that just ON and OFF status.

A further object is to provide a transducer in the form of a strain gauge, for compactness.

An additional object is to provide pulse producing circuitry contained by the body structure, and operable to produce a series of detectable pulses which have durations that increase as the amplitude of body squeeze force increases. Such pulse durations may have maximum durations when a predetermined threshold level of squeeze is exerted. Also, each pulse may comprise a series of vibrating oscillations at a first predetermined frequency $f_1$.

A further object is to provide circuitry that produces such pulses, and that comprises:

i) a first group of pulses each of which comprises a series of vibrating oscillations at a first predetermined frequency $f_1$ the pulses of this first group having maximum duration when a predetermined threshold level of squeeze is exerted, and j) a second group of pulses each of which comprises a series of vibrating oscillations at a second predetermined frequency $f_2$, the pulses of the second group produced only after said squeeze exceeds said threshold level.

Additional objects include provision of a carrier on which the exerciser is supported and via which squeeze force is transmitted to said body structure; and in this regard the carrier may comprise one of the following:

i) a briefcase handle or strap ii) a handle of a tennis racket iii) a steering element or part iv) a tensioner handle v) a headrest.

These and other objects and advantages of the invention, as well as the details of an illustrative embodiment, will be more fully understood from the following specification and drawings, in which:

DETAILED DESCRIPTION

Figure 18:
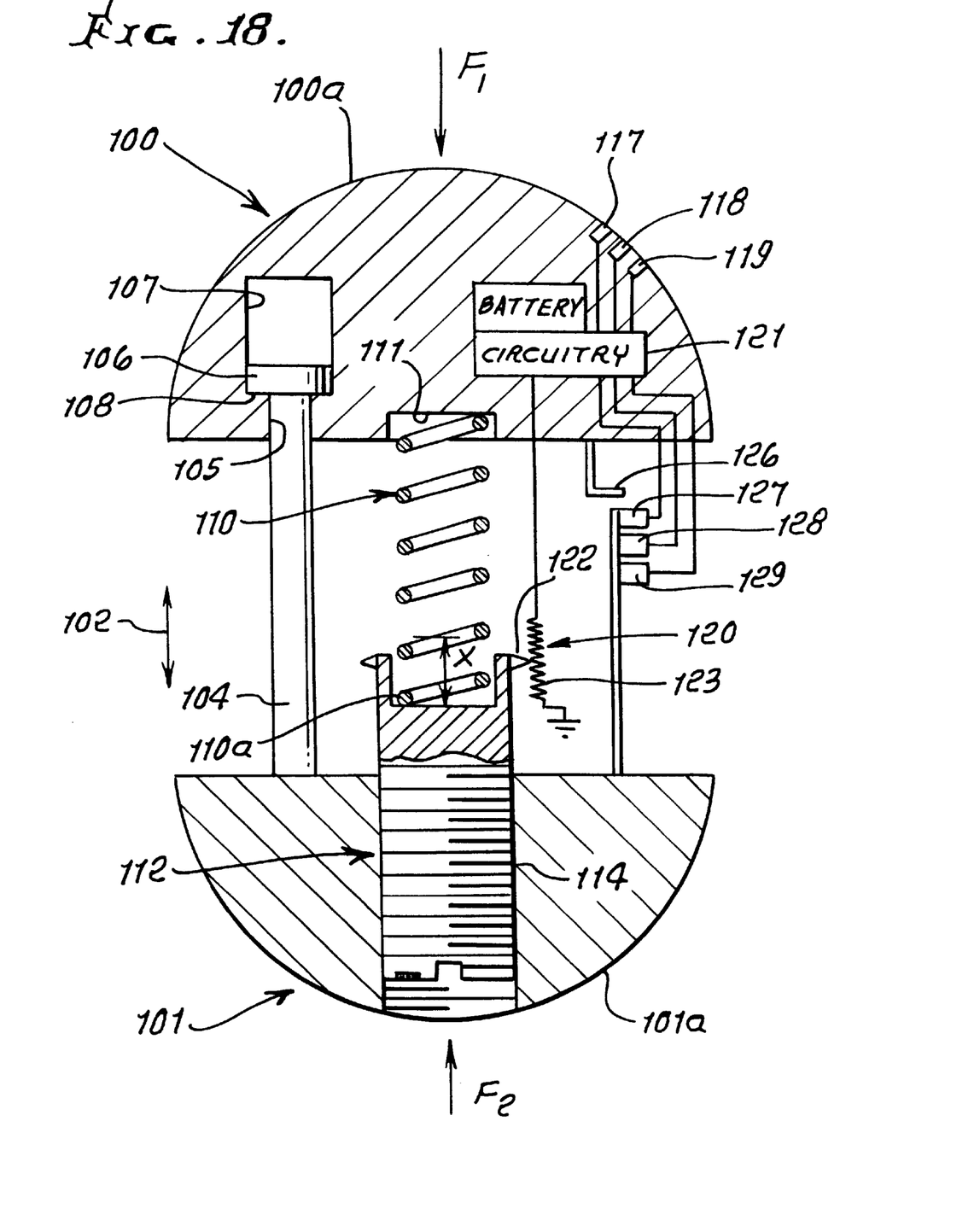
FIG. 18 is a schematic design.

Referring first to FIG. 18, it shows in schematic form the overall organization. Upper and lower bodies 100 and 101 have convex surfaces 100a and 101a to be hand grasped. The bodies are movable toward and away from one another, in directions indicated by arrows 102. Force is applicable as indicated by arrows $F_1$ and $F_2$.

A vertical guide 104 projects upwardly between the bodies from lower body 101. It slidably guides in bore 105 in body 100. An enlarged stop 106 on the guide is movable in bore 107, and the stop engages upper body shoulder 108 to limit relative separation of the bodies.

A spring, for example a compression spring 110, extends between the bodies, and has an upper end that engages upper body shoulder 111. The spring lower end 110a is carried by an adjuster 112 which has relatively long-lead, threaded engagement with body 101, at 114. (One 360° turn of the adjuster lifts the spring lower end by amount X.) As the adjuster is rotated, the spring is tightened or loosened to vary the spring force acting to separate the bodies 100 and 101. Therefore, the amount of force $F_1$ and or $F_2$ required to urge the bodies relatively together may be adjusted. The user can determine the position of the adjuster, as by observing the rotary position of a marker 115 on the lower end of the adjuster. If desired, the adjuster rotary position can be electrically indicated as by ON or OFF indication of LEDs 117–119 on body 100. Control of the LEDs is afforded by a potentimeter 120 and circuitry 121. The potentimeter annular wiper 122 is carried by adjuster 112, and vertical resistor 123 by upper body 100. As the adjuster is rotated, the wiper moves upwardly or downwardly against the resistor, to vary the voltage input to circuit 121, which in turn controls varied illumination of the LEDs, prior to urging of the bodies 100 and 101 toward one another.

The extent of squeeze displacement of the bodies toward one another can also be detected, and indicated. Note the contact 126 carried by the upper body for successive engagement with contacts 127–129 carried by the lower body 101, contacts 127–129 arranged in a row in the direction of relative body movement. The intensity of illumination output of the LEDs can, for example be indicated, in response to such body movement and stepwise engagement of contact 126 with contacts 127–129. Annunciators can be substituted for the LEDs, to provide desired audible pulsing or vibration. Elements 127–129 can be mechanical "click" producing, audible sounders, such as spring arms that are released to produce sound.

Referring next to FIGS. 1–4, the exerciser 100 in its preferred form incorporates a longitudinally horizontally elongated upper handle part 10 extending parallel to, over, and spaced from a longitudinally horizontally elongated bottom handle part 11, so that the two parts can be squeezed, one toward the other, for example vertically. Part 10 has an elongated, upwardly convex surface 10a merging with side surfaces 10b and 10c, for ease of manual grasping, and a flat lower surface 10d facing lower part 11. That lower part 11 is elongated beneath part 10, and has a horizontally flat local upper surface 11a, and downwardly rounded, i.e. convex sides 11b and 11c. There are upwardly projecting longitudinally spaced end flanges 10e and 10f on upper part 10, and longitudinally spaced downwardly spaced end flanges 11e and 11f on lower part 11. These provide device support surfaces as at 10g and 11g, and which are downwardly flat.

A bottom 11d' between end flanges 11g is shown and is downwardly convex, for ease of hand grasping. Opposite ends of bodies 10 and 11 appear at 10h and 10i, and 11h and 11i.

The force F (squeeze) with which the top part 10 is forced toward the bottom part 11 is the force exerted by the operator. (Note that directional words "top, bottom, up, down, left, right" are used here to clarify the figures, not to indicate a preferred orientation of use.) A slide 12 is movable longitudinally left or right in a body recess 13, by the operator, to select relative to scale 14 the desired value of F where feedback to the operator occurs. Note slide marker 12a, and a block 83 connected to the slide to vary the effective length of a cantilever spring beam 28.

The flat bottom surfaces 11g of flanges 11e and 11f facilitate use when the force relates to that occurring when the human user pushes down on 10 while 11 is set against a flat surface. When the exerciser is used for squeezing by a hand, the hand (either palm or finger) fits on the curved, downward convex bottom 11d' between the square end flanges, and also over the upward convex top 10a, i.e. the device is hand held.

Figure 4:
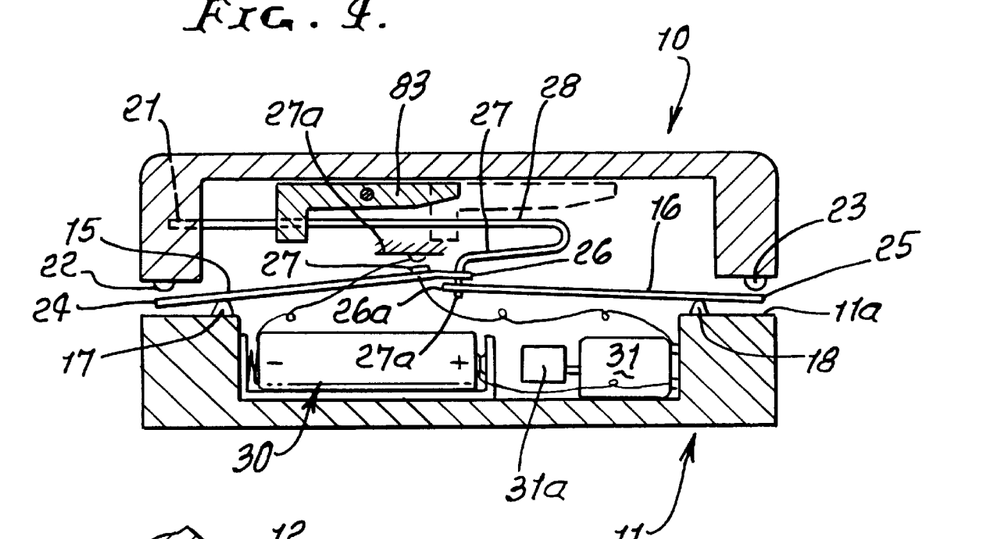
FIG. 4 is a vertical longitudinal section taken on lines 4—4 of FIG. 1.
Figure 7:
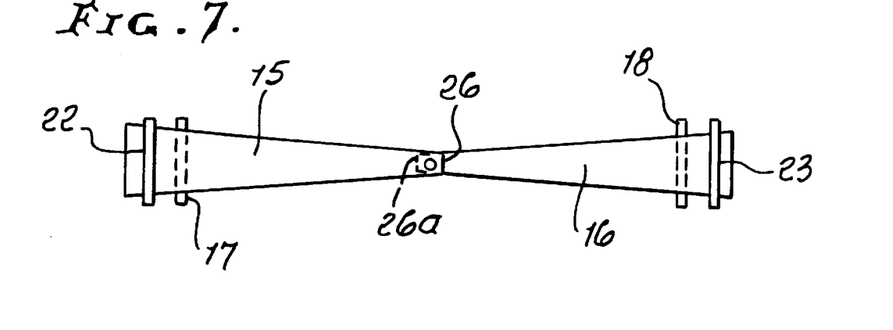
FIG. 7 is a plan view of levers used in FIGS. 1–6.

FIGS. 4 and 7 show the interconnection and operation of the parts. The moving levers 15 and 16 pivot about fulcrums 17 and 18 on the top surface 11a of lower part 11. The pushers 22 and 23 on upper part 10 move downwardly onto lever extensions 24 and 25 carried by levers 15 and 16, and thereby transmit force from 10 to the ends of levers 15 and 16, which are upwardly and downwardly movable with part 10. At 26 and 26a the overlapping other ends of the levers, the force on each lever has been substantially reduced, as for example by a factor of 8 to 10, and the vertical motion increased correspondingly, because of the proportions of the levers. A short wire 27a is loosely held in holes at the lever ends 26 and 26a so that the vertical force on a tab 27 is the sum of the vertical forces exerted by levers 15 and 16 where they overlap.

Figure 2:
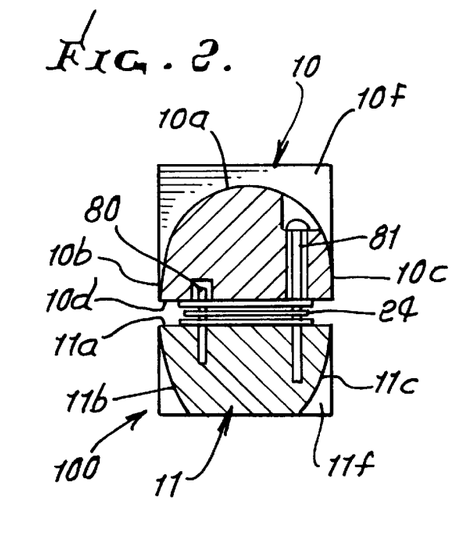
FIG. 2 is a section taken on lines 2—2 of FIG. 1.

The distance that tab 27 moves up is that amount permitted by restraining cantilever beam 28 mounted to part 10 at 21 as shown. Tab 27 and beam 28 may consist of a spring wire, configured with a U-bend as shown. As selector slide 12 is moved left and right, the spring characteristic of cantilever restraining beam 28 is modified because the effective length of the free bending part of the restraining beam is altered. Thus, the slide is operatively and variably coupled to 28. When the restraining beam 28 is moved up by the levers to cause a contact 27 on lever 15 to touch the electric contact 27a on part 10, an electric circuit connects the batteries 30 to a motor 31. Rotation of an eccentric weight 31a on the shaft of 31 causes a vibration throughout the exerciser, as readily felt by the operator, i.e. indicated, until the squeeze force is decreased enough to disconnect the contact at 27a. Note that with the geometry as shown, the summing of forces by the linked levers 15 and 16 causes the completion of the electric circuit for a specific position of slide 12 wherever the forces are applied to 10: left end of 10, right end of 10, or distributed across 10, as long as the positions are no further out than shafts 22 and 23. FIG. 2 shows use of guides 81, like guide 104 in FIG. 18. Parts 10 and 11 are hollow, to contain the mechanism shown.

Figure 16:
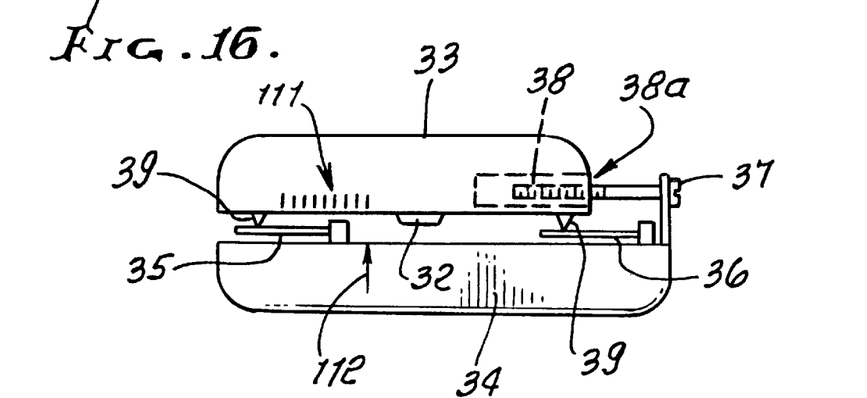
FIGS. 16 and 17 are views like FIG. 4, but showing modifications.

FIG. 16 shows another way to move a force sensor 32 (affixed to a top body 33) downward to where it contacts a bottom body 34 when the selected compressive force i.e. squeeze is applied to 33 and 34. Flexible cantilever arms 35 and 36 are rigidly mounted at their right ends to lower body 34. When adjustment knob 37 is turned, the attached screw 38, through nut 38a affixed to upper body 33, moves body 33 with its contact pawls 39 to the right, where a greater force is required to be exerted via supports 39 to bend spring beams 35 and 36 enough to allow 32 to touch 34. The scale marks at 111 on body 33, that line up against the indicator arrow 112 on 34, are positioned by calibration, to show the applied force needed for contact.

Figure 17:
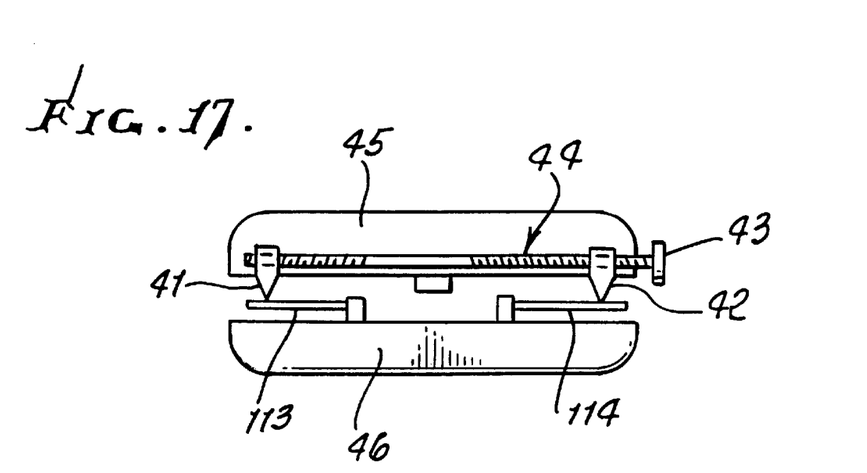

FIG. 17 shows a symmetrical alternative to FIG. 16. Instead of moving the top body 45 left and right along or lengthwise of the bottom body 46, the pawls contact the flexible lever arms 113 and 114 (extending oppositely) closer to or further from their rigid supported ends, and thus change the effective force vs vertical distance sensitivity of the force sensor. In FIG. 17 the pawls 41 and 42 are moved symmetrically oppositely toward or away from the center by rotating knob 43 that connects to the long screw 44 that has clockwise threads on its left half to move pawl 41, and anti-clockwise threads on its right half to move pawl 42. The position of one or both pawls on upper body 45 can be seen from the outside, and correspond to a particular sensitivity for the force required to make the force sensor operate.

Note that the principles behind the FIG. 16 and 17 units are that the relationship between the applied force and the vertical displacement of the force sensor 32 is varied by the position variation of the pawls along the flexible arms, such as 35 and 36. By way of contrast, in FIGS. 1–4, the two beams or levers 15 and 16 amplify the downward motion transmitted by the upper body 10 as it descends toward the lower body 11 to become a much larger vertical motion exerted against beam 28. There are two advantages: displacement of the sensor is increased so manufacturing tolerances become less tight, and the force on slender beam or arm 28 is much less then the direct pawl forces on the rugged flexible arms of FIGS. 16 and 17, and so there is less danger of permanent set of the flexible arm or beam 28.

Figure 3:
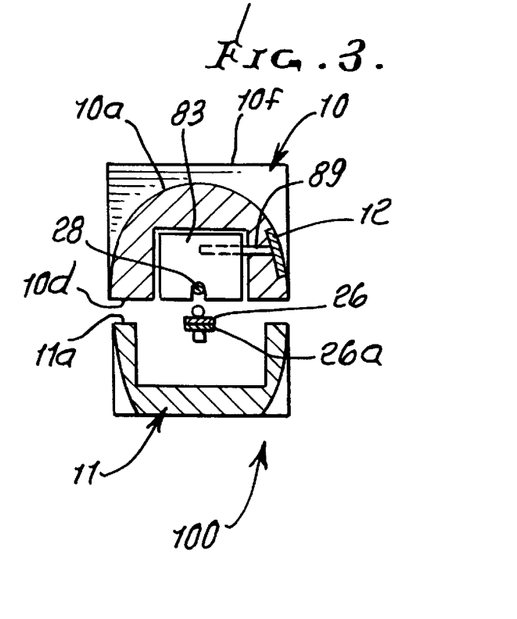
FIG. 3 is a section taken on line 3—3 of FIG. 1.
Figure 5:
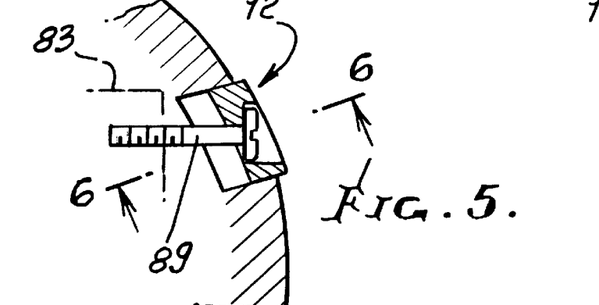
FIG. 5 is an enlarged view showing in greater detail the adjustment seen in FIG. 3.
Figure 6:
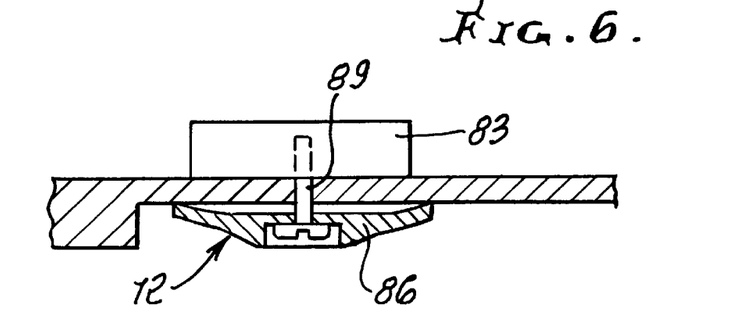
FIG. 6 is an enlarged view taken in section on lines 6—6 of FIG. 5 to show frictional sliding.
Figure 8:
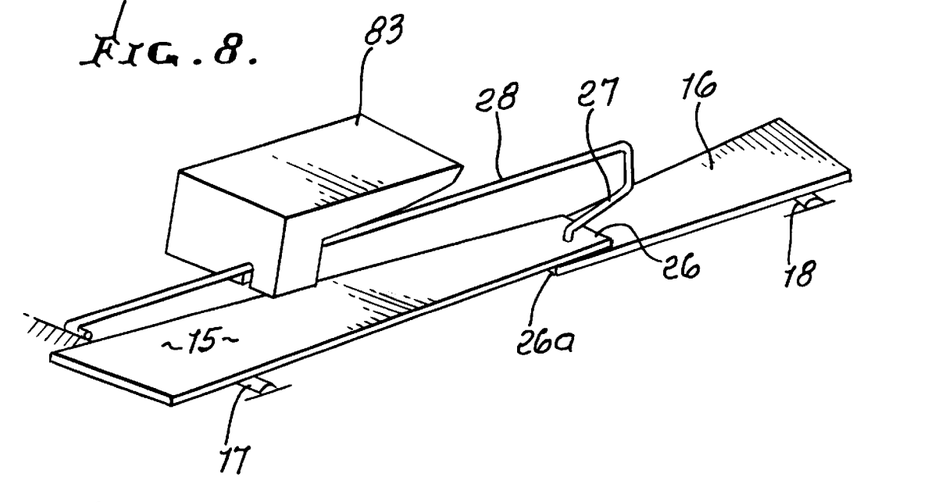
FIG. 8 is an isometric view showing internal construction.

Also shown in FIG. 2 are vertical guide or guides 80 and 81 to guide relative movement of bodies 10 and 11. FIGS. 3, 4 and 8 show sliding at 84 of block 83 along the beam 28. FIGS. 5 and 6 show frictional sliding of a bowed part 86 associated with block 83, and connection at 89 to the slide 12, to locate the slide and block, at selected positions.

Figure 9:
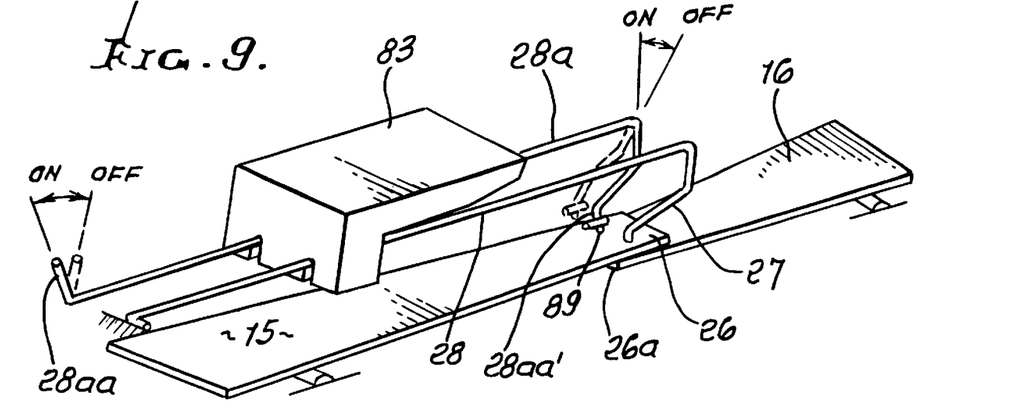
FIG. 9 is a view like FIG. 8 but showing a modification.
Figure 10:
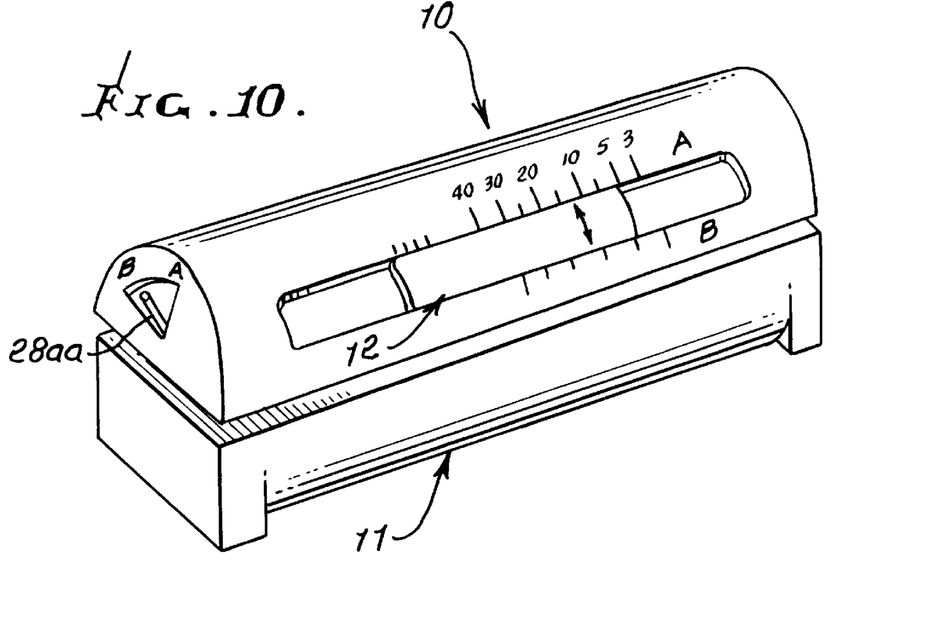
FIG. 10 is a view like FIG. 1, but incorporating the FIG. 9 modification.

FIGS. 9 and 10 show optional use of a second beam or wire 28a operatively connected to the slider block 83 and optionally connectible to the levers 15 and 16. Therefore, if a stepwise greater spring resistance to closing together of the parts 10 and 11 is desired, wire 28a is rotated about its axis as by a bent end 28aa of that wire, to bring arm 28aa' of the wire into slots 89 in the ends 26 and 26a of the two levers. Now both wires 28 and 28a resist upward deflection of the lever ends. Bent end 28aa may protrude at the rear wall 10h, for rotation between positions A and B, as indicated.

Figure 11:
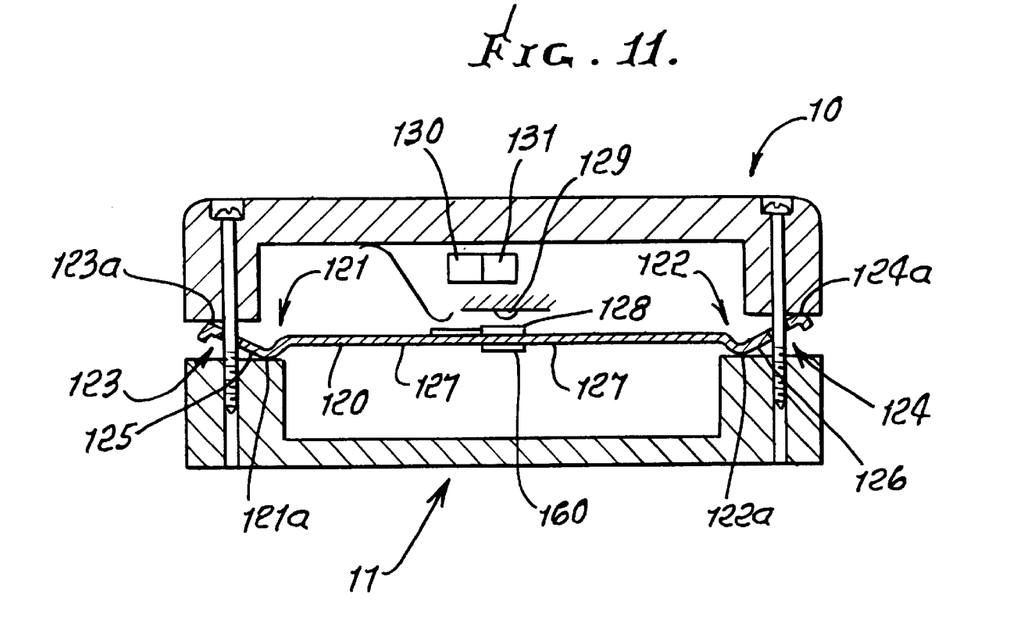
FIG. 11 is a view like FIG. 4, but showing a Modified internal construction.
Figure 12:
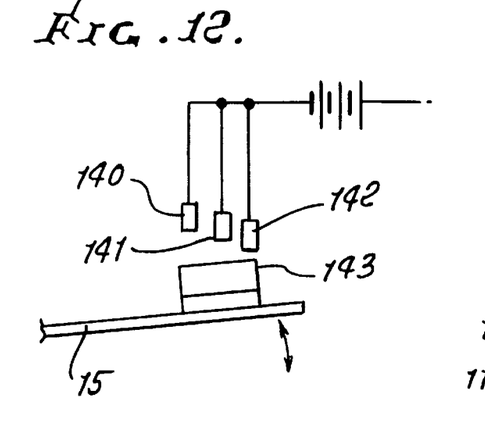
FIG. 12 is a schematic view showing multiple connections, for different feed backs, at different percentages of selected load.
Figure 13:
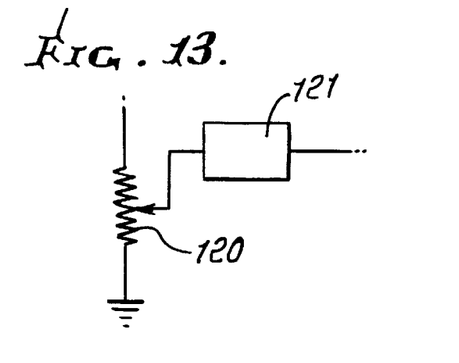
FIG. 13 is a circuit diagram.

FIG. 11 shows an alternate form of the device in which one elongated spring arm 120 is substituted for levers 15 and 16. Arm 120 has downward protrusions at 121 and 122 to engage the bottom part 11 at 121a and 122a, and upward protrusions 123 and 124 to engage the upper part 10 at 123a and 124a. As upper handle part 10 is pushed downwardly, the arm 120 flexes downwardly at 125 and 126, and upwardly at mid-extent 127, where a strain gauge (as represented at 160) may be employed, with output connected to 130 (see below). Alternatively a contact 128 on 127 may be used to engage contact 129 on upper part 10, causing circuitry 130 to activate an annunciator or vibrator 131 as referred to above. FIG. 12 shows three different contacts 140–142 to be successively engaged by a contact 143, as the parts 10 and 11 move relatively together. (See in this regard, FIG. 18, contacts 127–129 engagable by contact 126, to offset output.) FIG. 13 is a circuit diagram as also seen in FIG. 18.

Figure 1:
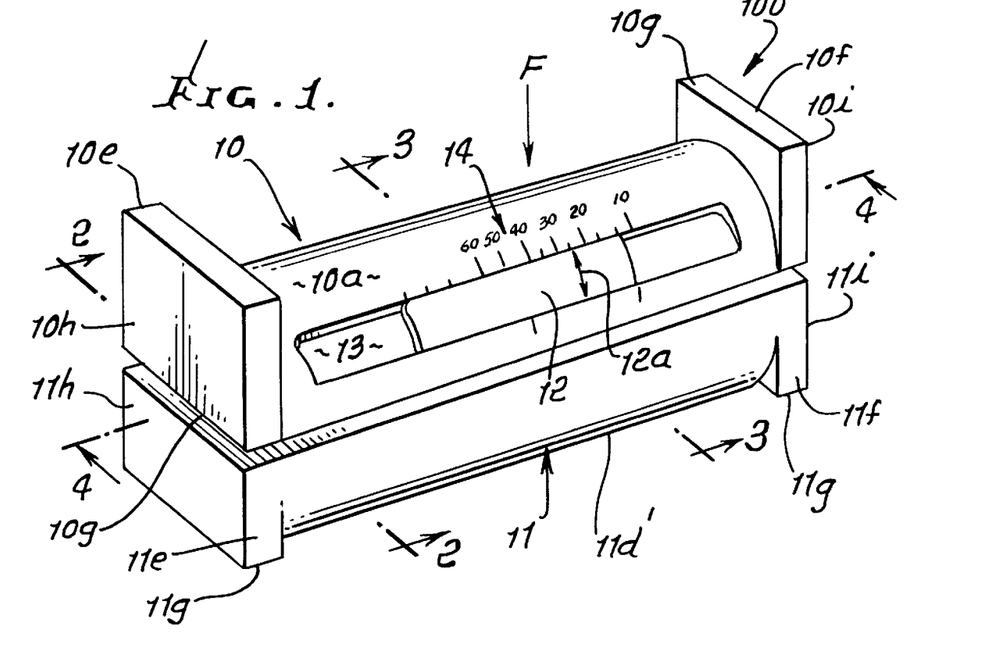
FIG. 1 is an isometric view showing one form of exerciser incorporating the invention.
Figure 14:
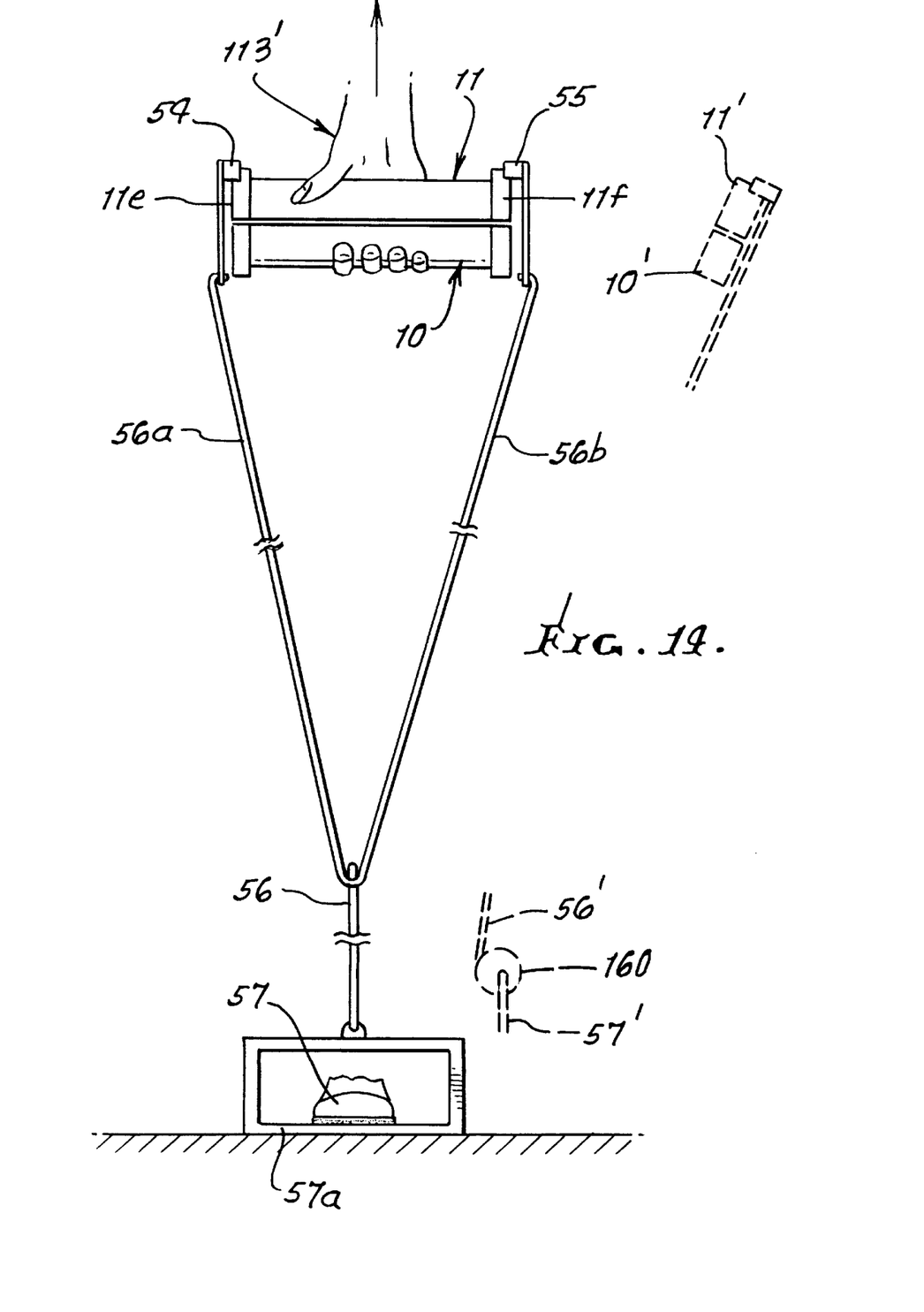
FIG. 14 shows an application of the hand squeezable device to a cord.
Figure 14A:
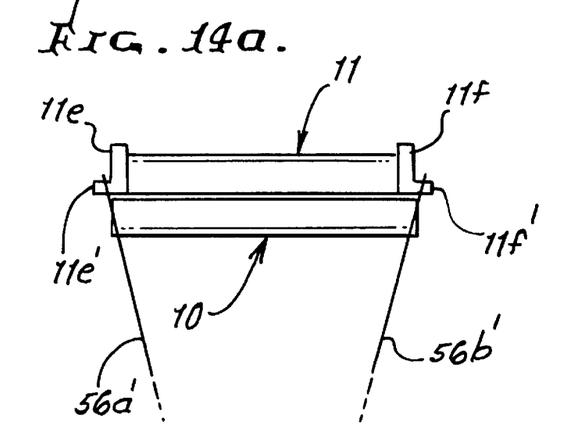
FIG. 14a shows a modification.

FIG. 14 shows two clips 54 and 55 that fit snugly on the flange portions 11e and 11f of the bottom body 11 of the inverted unit as seen in FIG. 1. Strap 56 is connected to the clips via strap extensions 56a and 56b. By holding a foot 57 on the loop 57a at the bottom of strap 56, the upward force exerted by hand 113' on body 10 can be applied at a convenient location i.e. 10 and 11 can be swung to alternate positions at seen at 10' and 11'. Strap 56 can be flexible or non flexible. FIG. 14a shows a modification in which ears 11e' and 11f' are provided on 11e and 11f, to support flexible lines 56a' and 56b' corresponding to 56a and 56b in FIG. 14, simplifying the arrangement, as by eliminating need for clips 54 and 55 and straps 56a and 56b.

Figure 15A:
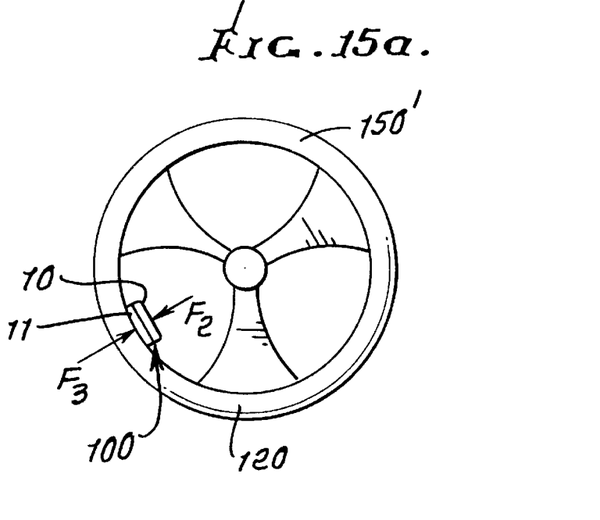
FIG. 15a shows device application to a steering wheel.
Figure 15B:
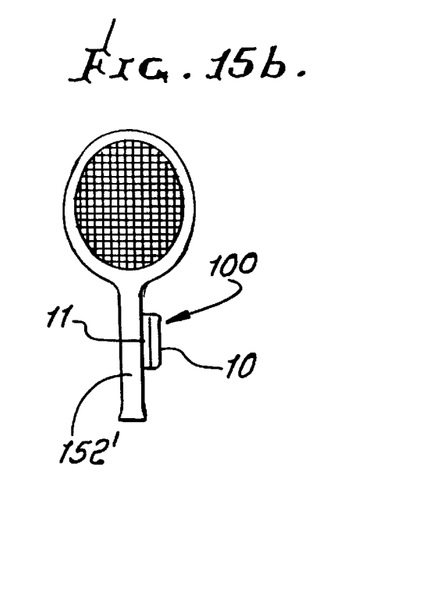
FIG. 15b shows device application to a tennis racket.
Figure 15C:
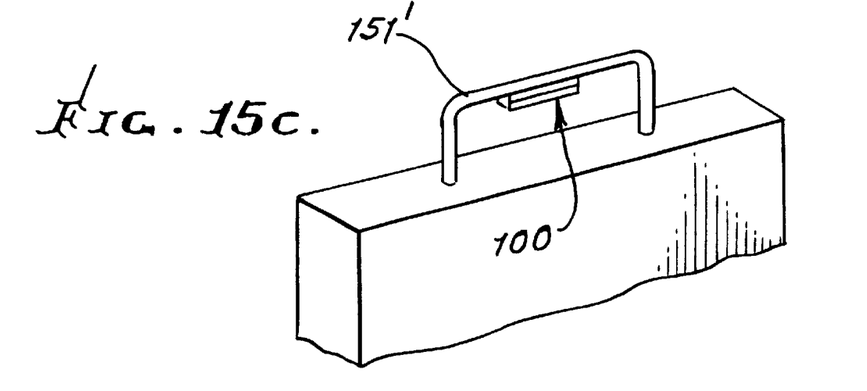
FIG. 15c shows device application to a briefcase handle.

FIGS. 15a–15c clarify and depict typical uses to which the isometric experience can be put.

FIG. 15a shows the bottom part 11 of the exerciser 100 mounted on a carrier 120 so that the user can squeeze body parts 10 and 11 via the carrier, as via squeeze force application shown at $F_2$ and $F_3$. The carrier can, for example be one of the following:

i) a steering element 150' of a craft such as a vehicle, boat, aircraft, etc.

ii) a briefcase strap, as seen at 151' in FIG. 15c iii) the handle 152' of a tennis racket, as seen in FIG. 15b iv) a tensioner handle v) a headrest (in which case $F_2$ represents head force, the carrier being fixed).

The exerted force can be a function of velocity of upward pull, i.e. $F=f(v^n)$, where "n" is a variable determined by the mechanism. For example, a device such as a roller may be interposed between strap 56 and loop 57, with a return spring attached to the roller. See elements 160, 56' and 57'.

Figure 19:
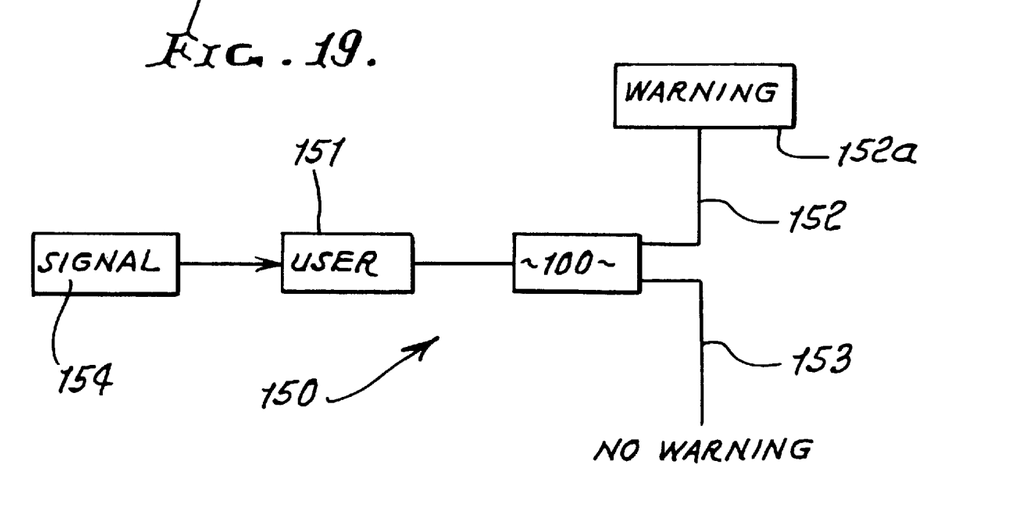
FIGS. 19 and 19a are system block diagrams.

FIG. 19 shows use of the device 100 in a warning system indicated at 150, in block diagram form. A user 151, such as a vehicle driver, has his hand in a position to squeeze the device 150. That device is adjusted to effect production of a warning signal, indicated at output 152, if the user fails to exert sufficient squeeze force after a suitable time interval, say five seconds. If he does not exert sufficient squeeze force, no warning is produced, as indicated at 153.

An input signal is provided or generated at 154. That signal may for example be an audible "BEEP" produced at repetitive intervals, say every six seconds. Thus, the sleepy operator is reminded to squeeze the device every six seconds at a squeeze force level consistent with being awake. If he fails to do so, a loud warning is produced, as at 152a to awaken him.

Figure 19A:
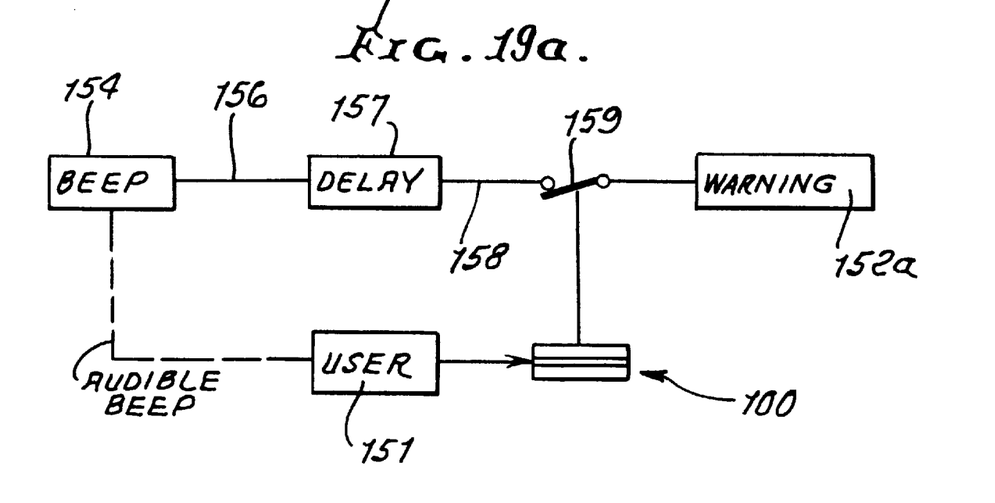

FIG. 19a shows a circuit to provide the FIG. 19 functions. When signal generator 154 provides an audible BEEP signal to the user 151, it also sends a pulse at 156 to a delay circuit 157. After a time interval t, say six seconds, delay circuit 157 sends a pulse on line 158 to activate the WARNING producing device 152a. A switch 159 in line 158 can be opened by squeezing of device 150 above a selected squeeze force level. If the user fails to sufficiently squeeze device 150, switch 159 is not opened, and the WARNING is produced, at repetitive intervals t.

Additional advantages of the device of the invention are:

Small, fits in pocket or purse so user always has close access to device, with convenience of not having to go to an exercise facility;

Device can be the handle of a briefcase, to give the traveling user an exercise opportunity;

Device is adaptable to a vehicle steering wheel, a tennis racket handle, and to a neck rest in a vehicle.

User has many force scale options: linear, non-linear, and multiple;

User has many feedback options: sound, light, telemeter signal to a TV at which user is already looking, vibration (or jolt or sudden slip);

Exercise involves at least one user's body part touching the device, and therefore the vibration feedback can always be detected by that body part; note that simple vibration is quieter than audible sound, and thus less annoying to others. (Vibration is of course always related to some sound.)

Provision for many mechanism options: springs, levers, on-off switch, strain gauges;

Device may exhibit various colors, different sizes for different people;

More sophisticated electronics can for example give a special identity to the tenth repetition at one strength setting, (such as stronger vibration, or rapid on-off-on-off-etc.).

The device can be combined with a pull cord whose rate of pulling determines its force level as referred to in FIG. 14; i.e. F=f(v"). The device itself can be the puller handle. The user pulls at a rate that resists the pull at the device force setting. This simple mechanism can substitute for weight lifts (mechanism held down by user's foot) or weight pull down (mechanism bracket attached to top of a door). A curtain roller is a good starting point.

Many feedback options, beside ON-OFF. For use with a tennis racket, device is "OFF" when zero or small force is applied; FULL ON when inadequate force is applied; zero again when force is correct. For basic exerciser, 400 HZ pulses can start at 80% of a selected force, with a pulse ON 0.1 sec., OFF 0.9, or 0.1 sec., etc. at 88% attainment of selected force, a pulse is ON 0.5 sec., OFF 0.5 sec.; at 96% of exertion force, device is ON continually; above 100%, vibrator operates at 800 Hz, and above 104% vibration interrupted every 1 second as, with the 80% to 96% realm but now with shorter "ON" periods. No signal provided above 120 or 125%. This is by way of example, only.

Force selection can be made by push button or other device; an output display can be alphanumeric, or by means of length of an electronic bar display.

For the unit connected to the electric cable, for some exercises, the cable can be non-elastic (standard rope or cord).

The unit rounded shape is comfortable to hold or to press one side against a human body/arm/leg/ or other internal or external surface. Flat sections or flanges at opposite ends stabilize the unit when it is pressed against a flat surface such as a wall or table. The flat sections may be omitted. An alternative would be to eliminate the flats at each end, and to flatten the base (underside) of the oval cross-section to permit stable pushing against a flat surface. The squared ends provide a convenient structure onto which to clip the ends of an elastic cord that sometimes is employed during exercising. Other simple attachment options are available.

Additional features are as follows:

There can be multiple scales or ranges for the selected forces on the exerciser. There can be supplementary equipment such as a stretchable cord whose ends clip onto an exerciser that provides a resistive force against which the device, as a "handle", is moved. The exerciser can be built into the steering wheel of a car so that exercises can be conducted while driving: hand squeezes of the two units on the right and left segments of the steering wheel; compression or separation forces between the two units. Note that the hands must be firmly holding onto the steering wheel for this application, for applying the forces and receiving vibration feedback—and the firm grip can improve driving safety. Exercisers can also be integrated into the car seat or headrest, to quantify other in-car exercises.

There are also various approaches to the technical specifics of the device. It is important that the compressive force be sensed accurately wherever it is applied laterally along the device. Linkages bring the applied force to a common point where the sensing takes place (or, more expensive, multiple sensing at the periphery is summed). The simple device employs two levers that meet in the middle of the unit where the compressive forces from the ends are summed (after being decreased by, say 10 times). The force is monitored by the displacement at the center against a spring. The spring tension is typically adjustable, in a non-linear manner, by the spring being a wire or beam whose effective length is adjusted by a slide guide. (The amount of non-linearity is readily adjusted by adjusting the percentage of wire length through which the slide moves. The force for a specific deflection of the beam end varies as the cube of beam length. Decreasing the beam length by 50% gives a convenient non-linearity. To have a desirable long slide adjustment results in a long wire, but the free end is doubled back to reach the swing point and so the overall length is left small enough to fit in the unit.)

Instead of a two-lever system a single sensing bean connecting to the two ends can be used, with a strain gauge at mid-beam sensing the summed loads from each end. (Actually, the strain gauges are used, one above and one below the beam, to compensate for temperature effects.) The strain gauge output can be compared against the output of a user adjustable resistor (conveniently built into one end of the unit) calibrated so the selected force is indicated by position of a knob. The resistor can be a non-linear type. With a more flexible beam, the single beam approach can be substituted for the two levers of the simple or reference device.

Referring again to FIGS. 8 and 11, the circuitry shown at 121 and 131 may include pulse producing circuitry operable to produce a series of detectable pulses which have durations that increase or decrease as the amplitude of squeeze increases. Such pulse durations may have maximum duration when a predetermined threshold level of squeeze is exerted. Each pulse may comprise a series of vibrating oscillations at a first predetermined frequency $f_1$.

Further, the pulse may comprise i) a first group of pulses each of which comprises a series of vibrating oscillations at a first predetermined frequency $f_1$ the pulses of this first group having maximum duration when a predetermined threshold level of squeeze is exerted, and j) a second group of pulses each of which comprises a series of vibrating oscillations at a second predetermined frequency $f_2$, the pulses of the second group produced only after said squeeze exceedsd the threshold level.

I claim:

1. A squeezable exerciser comprising in combination
  a) body structure having surfaces to be squeezed relatively toward one another by application of force exerted by a user,
  b) first means associated with said body structure to produce a reference signal or signals as the level of force application reaches a preset limit or limits,
  c) and adjusting means to continuously and variably adjust the threshold level of force application at which said reference signal or signals are produced,
  d) said first means including electrical circuitry including a transducer,
  e) said transducer including an electrical contact, and there being at least one spring yieldably resisting movement of said contact in response to said squeezing,
  f) said first means including at least one lever acting to displace said contact at a locus characterized in that squeeze displacement is substantially less than contact displacement.

2. The combination of claim 1 wherein said means produces said signal or signal as said force level increases.

3. The combination of claim 1 wherein said first means is contained by said body structure.

4. The combination of claim 1 wherein said adjusting means includes a member which is manually adjustable to adjust the threshold level of force application at which said signal or signals are detectable.

5. The combination of claim 1 wherein said body structure includes two elongated bodies interconnected to be relatively squeezed toward one another.

6. The combination of claim 1 wherein said spring is an elongated cantilever spring.

7. The combination of claim 6 wherein said spring, contact and transducer are contained by said body structure.

8. The combination of claim 1 wherein said lever has a fulcrum and receives squeeze force at a lever location closer to said fulcrum than said contact.

9. The combination of claim 1 wherein said first means includes two levers acting to displace said contact and extending relatively oppositely from said contact.

10. The combination of claim 9 wherein each lever has a fulcrum and receives squeeze force at a lever location closer to said fulcrum than said contact.

11. The combination of claim 10 wherein said spring is an elongated cantilever spring extending generally parallel to said levers.

12. The combination of claim 11 wherein said spring is U-shaped and has a return bend portion resisting movement of said contact, in response to said squeezing.

13. The combination of claim 12 wherein said spring is a wire.

14. A squeezable exerciser comprising in combination
  a) body structure having surfaces to be squeezed relatively toward one another by application of force exerted by user,
  b) and means associated with said body structure to produce a reference signal or signals as the level of force application reaches a preset limit or limits,
  c) said means includes electrical circuitry including a transducer,
  d) said transducer includes an electrical contact, and said means includes at least one spring yieldably resisting movement of said contact in response to said squeezing,
  e) said means includes two levers acting to displace said contact and extending relatively oppositely from said contact,
  f) wherein each lever has a fulcrum and receives squeeze force at a lever location closer to said fulcrum than said contact,
  g) said spring is an elongated cantilever spring extending generally parallel to said levers,
  h) said spring is U-shaped and has a return bend portion resisting movement of said contact, in response to said squeezing,
  i) said spring is a wire,
  j) and wherein said means includes a member which is coupled to said wire and is manually adjustable in a direction parallel to the wire length to adjustably inhibit wire bending, thereby to adjust the threshold level of force application at which said reference signal or signals are produced.

15. The combination of claim 1 wherein said transducer comprises a strain gauge.

16. The combination of claim 15 wherein said first means includes an element carrying the transducer and carried to bend in response to squeeze exertion on said body structure.

17. The combination of claim 1 wherein said circuitry includes pulse producing circuitry operable to produce a series of detectable pulses which have durations that increase or decrease as the amplitude of said squeeze increases.

18. The combination of claim 17 wherein said pulse durations have maximum durations when a predetermined threshold level of squeeze is exerted.

19. The combination of claim 17 wherein each pulse comprises a series of vibrating oscillations at a first predetermined frequency $f_1$.

20. The combination of claim 17 wherein the pulses comprise i) a first group of pulses each of which comprises a series of vibrating oscillations at a first predetermined frequency $f_1$ the pulses of this first group having maximum duration when a predetermined threshold level of squeeze is exerted, and j) a second group of pulses each of which comprises a series of vibrating oscillations at a second predetermined frequency $f_2$, the pulses of the second group produced only after said squeeze exceeds said threshold level.

21. The combination of claim 1 including a carrier on which said exerciser is supported and via which squeeze is transmitted to said body structure.

22. The combination of claim 21 wherein said carrier is one of the following:

i) a briefcase handle or strap ii) a handle of a tennis racket iii) a steering wheel iv) a tensioner handle v) a headrest.

23. The combination of claim 1 including feedback means including a gripping force sensor and means to produce vibration in said body structure in response to operation of said sensor, and at a characteristic mode to be detected by the user when gripping force applied by the user exceeds a threshold level, there being adjusting means on said body structure to adjust said threshold level.

24. The combination of claim 23 wherein said body structure includes two bodies that are elongated, one body overlying the other to be squeezed toward said other body.

25. The combination of claim 24 including a surface on one body to stably engage a support as one body is pushed relatively toward the other body.

26. The combination of claim 23 wherein said adjusting means includes a manually adjustable slide element movable generally linearly.

27. The combination of claim 1 including a WARNING indicator on the body structure to produce a warning output if the level of force application fails to reach a preset limit or limits.

28. The combination of claim 1 including line structure operatively connected to said body structure for transmitting force to the body structure.

29. The combination of claim 28 including holder structure to which the line structure is operatively connected, whereby said force is transmitted by said line structure and between said holder structure and said body structure.

30. The combination of claim 29 wherein said holder structure is attached to said line structure and is configured to be retained to a fixed surface.

31. The combination of claim 30 wherein said holder structure extends along a looping path.

32. The combination of claim 29 including a roller, said line structure having a portion thereof entrained about said roller.

33. The combination of claim 5 including line structure operatively connected to opposite ends of one of said elongated bodies.

34. The combination of claim 5 including line structure having first, second and third sections, the first and second sections respectively connected to opposite ends of one of said elongated bodies, the third section operatively connected to both said first and second sections.

35. The combination of claim 34 including a roller, said line structure having a portion thereof entrained about said roller.

* * * * *